(12) United States Patent
Nöcker et al.

(10) Patent No.: US 10,398,914 B2
(45) Date of Patent: Sep. 3, 2019

(54) PROCESS FOR TREATING HAIR

(71) Applicant: KAO GERMANY GMBH, Darmstadt (DE)

(72) Inventors: Bernd Nöcker, Darmstadt (DE); Steven Breakspear, Darmstadt (DE); Peter Bauer, Darmstadt (DE); Manfred Dürr, Darmstadt (DE)

(73) Assignee: KAO GERMANY GMBH, Darmstadt (DE)

( * ) Notice: Subject to any disclaimer, the term of this patent is extended or adjusted under 35 U.S.C. 154(b) by 0 days.

(21) Appl. No.: 15/757,861

(22) PCT Filed: Mar. 15, 2016

(86) PCT No.: PCT/EP2016/055586
§ 371 (c)(1),
(2) Date: Mar. 6, 2018

(87) PCT Pub. No.: WO2017/041906
PCT Pub. Date: Mar. 16, 2017

(65) Prior Publication Data
US 2018/0326228 A1    Nov. 15, 2018

(30) Foreign Application Priority Data
Sep. 8, 2015   (EP) .................................... 15184314

(51) Int. Cl.
*A61Q 5/10* (2006.01)
*A61Q 5/08* (2006.01)
*A61K 8/362* (2006.01)
*A61K 8/44* (2006.01)

(52) U.S. Cl.
CPC ............... *A61Q 5/08* (2013.01); *A61K 8/362* (2013.01); *A61K 8/44* (2013.01); *A61Q 5/10* (2013.01)

(58) Field of Classification Search
CPC . A61Q 5/10; A61Q 8/22; A61K 8/411; A61K 8/415; A61K 8/19; A61K 2800/882; A61K 2800/884; A61K 8/361; A61K 2800/31; A61K 2800/4324; A61K 2800/88

See application file for complete search history.

(56) References Cited

U.S. PATENT DOCUMENTS

| 2002/0189034 A1 | 12/2002 | Kitabata et al. |
| 2004/0086475 A1 | 5/2004 | Boswell et al. |
| 2011/0203605 A1 * | 8/2011 | Allard ...................... A61K 8/23 132/208 |
| 2015/0034119 A1 | 2/2015 | Pressly et al. |
| 2015/0037270 A1 | 2/2015 | Pressly et al. |

FOREIGN PATENT DOCUMENTS

| EP | 1 602 356 A1 | 12/2005 |
| EP | 2 471 502 A1 | 7/2012 |
| EP | 2 883 530 A1 | 6/2015 |
| WO | 2015/017768 A1 | 2/2015 |

OTHER PUBLICATIONS

International Search Report dated Apr. 12, 2016, dated Apr. 20, 2016.

* cited by examiner

*Primary Examiner* — Eisa B Elhilo
(74) *Attorney, Agent, or Firm* — Norris McLaughlin, P.A.

(57) ABSTRACT

The present invention relates to a process for treating hair, especially human hair, wherein the hair is bleached and dyed in a subsequent order with compositions providing improved and milder bleaching and dyeing of hair. The inventors of the present invention have unexpectedly found out that when commonly used bleaching compositions and oxidative dyeing compositions are mixed with another composition comprising predominantly carboxylic acids, the bleaching and dyeing effects of the compositions are improved, homogeneous bleaching and dyeing of hair fibers is achieved and natural cosmetic properties of hair is maintained.

18 Claims, No Drawings

PROCESS FOR TREATING HAIR

This application is the U.S. National Stage of International Application No. PCT/EP2016/055586, filed Mar. 15, 2016, which claims foreign priority benefit under 35 U.S.C. § 119 of European Application No. EP15184314.1 filed Sep. 8, 2015 the disclosures of which are incorporated herein by reference.

The present invention relates to a process for treating hair, especially human hair, wherein the hair is bleached and dyed one after another with compositions providing improved and milder bleaching and dyeing of hair.

Bleaching human hair involves application of a strongly oxidative composition onto hair and leaving it for a certain period of time usually at elevated temperatures in order to oxidatively destroy the hair's natural melanin to lighten and/or completely remove the natural hair color. Since the process involves the use of strong oxidative compositions, the hair fiber itself is affected by such a treatment and therefore it also loses its certain natural properties such as its strength against breaking, its natural elasticity, its natural shine and natural soft feel upon touching.

On the other hand, oxidative dyeing of human hair has been used for many decades in order to permanently change the hair color. It involves application of a strongly oxidative composition comprising the dyestuff precursors and optionally coupling substances onto hair and leaving it for a certain period of time, usually at elevated temperatures, in order to allow for penetration of the relatively small uncolored dye precursors into the hair. In combination with the action of strong oxidizing agents, the dye precursors polymerize to larger molecules so that they may not be easily eluted from the hair fiber. At the same time the effect of the oxidizing agent is to lighten the hair color to provide a relatively homogeneous dyeing base.

Moreover, the to be bleached and dyed hair is not always homogeneous in its physicochemical status as it may be damaged due to previous chemical treatments such as dyeing and permanently shaping and/or environmental effects. This often leads to inhomogeneous bleaching and dyeing performance and, therefore, consumers' dissatisfaction. There is, therefore, a great need for milder and more effective bleaching and dyeing compositions which overcome one or more of the above mentioned problems.

Recently, in a series of patent applications (US2015/0034119, US2015/0037270, WO2015/017768), methods are published which claim benefits of the combined use of a bismaleate based binding agent in hair chemical treatments such as oxidative hair dyeing, permanently shaping and bleaching for improving hair structure. The publications are silent on the core of the present invention.

After a long research and careful considerations of the consumers' needs, the inventors of the present invention have unexpectedly found out that when commonly used bleaching compositions and oxidative dyeing compositions are mixed with another composition comprising predominantly carboxylic acids, the bleaching and dyeing effects of the compositions are improved, homogeneous bleaching and dyeing of hair fibers is achieved, color durability is enhanced, and natural cosmetic properties of hair is maintained.

Therefore, the first object of the present invention is a process for treating hair, especially human hair, comprising the following steps:
a. hair is applied an aqueous composition obtained from mixing two compositions A and B, wherein the composition A is an anhydrous composition comprising one or more persalts and one or more alkalizing agents,
wherein the composition B is an aqueous composition comprising one or more oxidizing agents, preferably hydrogen peroxide and has a pH in the range of 1.5 to 5, wherein the mixed composition consisting of compositions A and B has an alkaline pH in the range from 8 to 11,
b. the composition is left on the hair for a period of 1 min to 45 min,
c. the hair is rinsed off and towel dried,
d. optionally the hair is dried,
e. hair is applied another aqueous composition obtained from mixing the two compositions C and B wherein the composition C is an aqueous composition comprising one or more hair dyes and one or more alkalizing agents and has an alkaline pH preferably in the range of 7.5 to 12,
f. left on the hair for a period of 1 to 45 min,
g. rinsed off from the hair, and
h. hair is optionally washed with a cleansing composition and dried,
wherein the composition(s) in step(s) a and/or e is (are) mixed with a composition D immediately before application onto hair for obtaining ready-to-use composition(s), wherein the composition D comprises
i. one or more carboxylic acids and/or their salts having three or more carboxyl groups, and
ii. one or more organic additional acids and/or their salts having one or two carboxyl groups,
wherein the composition D comprises the acids of i) and ii) and/or their salts at a total concentration of 10% to 100% by weight calculated to the total of composition D,
wherein the ready-to-use compositions in steps a and d have a pH in the range from 6.5 to 11 and comprise the acids and/or their salts at a total concentration in the range from 1% to 10% by weight calculated to the total of each of the ready to use compositions.

The second object is a kit for hair, especially human hair, comprising the compositions A, B, C and D as defined above.

The term anhydrous means that the composition does not comprise any added water. It should be noted that one or more ingredients of the anhydrous composition may comprise bound crystal water or residual moisture which is not covered by the term.

The anhydrous composition A comprises one or more persalts. Useful are sodium persulfate and potassium persulfate and ammonium persulfate, earth alkali peroxides such as magnesium peroxide, melamine peroxide or urea peroxide or phthalimidoperoxy hexanoic acid. The preferred persalts are sodium persulfate and potassium persulfate. The persalt is comprised in the composition A at a total concentration in the range of 10% to 80%, preferably 15% to 70%, more preferably 20% to 60% and most preferably 25% to 60% by weight, calculated to the total of composition A.

According to the invention, the anhydrous composition can also comprise one or more ammonium salts at a concentration from 0.1% to 10% by weight calculated to the total of composition A. Suitable ammonium salts are ammonium carbonate, ammonium hydrogen carbonate, ammonium carbamate, ammonium chloride, ammonium sulfate, ammonium phosphates, ammonium nitrate, ammonium bromide, ammonium iodide, ammonium thiosulfate, ammonium molybdate, ammonium vanadate, ammonium sulfamate, ammonium citrate, ammonium salicylate, ammonium valerate, ammonium tartarate, ammonium benzoate, ammonium acetate, ammonium formiate and ammonium lactate. Compositions may also comprise mixtures of ammonium salts.

Preferred thereof are the ammonium phosphates, such as ammonium dihydrogen phopshate, diammonium hydrogen phosphate, diammonium sodium phosphate, ammonium sodium hydrogen phosphate or ammonium disodium phosphate, ammonium chloride, ammonium sulfate and diammonium hydrogen citrate.

The anhydrous composition A comprises one or more alkalizing agent(s). The preferred alkalizing agent is sodium metasilicate which is preferably comprised at a concentration from 1% to 20% by weight calculated to the total of composition A.

The composition B is an aqueous composition and comprises one or more oxidizing agent(s). The oxidizing agents suitable are hydrogen peroxide, urea peroxide, melamin peroxide or perborate salts. The most preferred is hydrogen peroxide. The composition B comprises one or more oxidizing agents at a total concentration of 1% to 20% by weight, preferably 2% to 15%, more preferably 2% to 12% and most preferably 3% to 12% by weight, calculated to the total of composition B. The composition B may be in the form of a solution, thickened gel or an emulsion. Emulsion form is particularly preferred.

The pH of the composition applied onto hair in step a, after mixing with composition D, is in the range of 6.5 to 11, preferably 8 to 11, more preferably 9 to 11 and most preferably 9 to 10.5.

After application of the aqueous composition obtained from mixing the compositions A, B and D (read below), it is left on the hair for a period of 1 min to 45 min at room temperature or at elevated temperatures up to 45° C. The hair is rinsed off and towel dried. The hair is optionally dried in case it is necessary for the performance of the dyeing composition to be applied.

The hair is applied another aqueous composition in step e of the process of the present invention obtained from mixing two compositions C and B which are further mixed prior to application onto hair with composition D.

The composition C comprises one or more hair dyes. Suitably, the composition C comprises one or more oxidative dye precursors, optionally one or more coupling substances, and optionally one or more direct dyes.

Suitable non-limiting examples of oxidative dye precursor classes are p-phenylendiamines, p-aminophenols, and heterocyclic compounds such as diaminopyrazols and substituted pyrimidines, and suitable coupling substances are resorcinols, m-aminophenols, m-phenylendiamines, pyridines, and naphthols.

Non-limiting examples of the oxidative dye precursor compounds are p-phenylenediamine, p-aminophenol, 2,5-diamino-toluene, 2-n-propyl or 2-ethyl-p-phenylenediamine, 2,6-di-methyl-p-phenylene-diamine, 2-(2,5-diaminophenyl) ethanol, 1-amino-4-bis-(2'-hydroxy-ethyl)aminobenzene, 2-(2-hydroxyethyl amino)-5-aminotoluene, 4,4'-diaminodiphenylamine, 4-aminodiphenylamine, 2-amino-5-N,N-diethyl aminotoluene, 4-amino-N-ethyl-N-isopropyl aniline, 2-chloro-p-phenylendiamine, 1-β-hydroxyethyl-2,5-diamino-4-chlorobenzene, 1-β-hydroxyethyl-2,5-diamino-4-methyl benzene, 2-methoxy-p-phenylenediamine, N,N-diethyl-p-phenylendiamine, 1-amino-4-β-methoxyethyl aminobenzene, 1-dimethyl-amino-4-aminobenzene, 1-hydroxy-2,5-diamino-4-methyl benzene, 1-hydroxymethyl-2,5-diaminobenzene, 1,3-dimethyl-2,5-diaminobenzene, 1,4-diamino isopropyl benzene and/or 1-amino-4-β-hydroxypropyl aminobenzene, 1-hydroxyethyl-4,5-diaminopyrazole, 3,4-diamino-5-hydroxypyrazole, 3,5-diaminopyrazole, 3,5-diamino pyrazol-1-carboxamide, 3-amino-5-hydroxypyrazole, 1-phenyl-2-methylpyrazole, 1-phenyl-3-methylpyrazole-5-one, 3,5-dimethylpyrazole, 3,5-dimethylpyrazole-1-methanol, 3,5-diamino-1,2,4-triazole, 4-aminophenol and the derivatives thereof such as 4-amino-3-methylphenol, 2-chloro-4-aminophenol, 2,6-dichloro-4-aminophenol, 2,4-diamino-phenol, 2,6-dibromo-4-aminophenol, tetraamino pyrimidines, triaminohydroxy pyrimidines, diaminomono- and -dihydroxy pyrimidines, aminotriazines, 5-amino salicylic acid and/or 1,2,4-triamino benzene, 2,5-diaminopyridine, 2,3-diaminopyridine, 2,6-diaminopyridine, 3-amino-2-methyl amino-6-methoxypyridine, 2-dimethyl-5-aminopyridine, 2-dimethyl aminoethyl-3-hydroxypyridine, 2-amino-4,6-dimethyl pyridine, 2-amino-3-hydroxypyridine, 3-amino-2(β-hydroxyethyl amino)-6-methoxy pyridine, 2,6-dimethyl amino-5-aminopyridine, 2-di(hydroxyethyl) amino-5-aminopyridine, 2-hydroxyethyl amino-5-aminopyridine, 4-hydroxy-2,5,6-triaminopyrimidine and/or the water-soluble salts thereof, and mixture thereof.

The total concentration of the dye precursors (developing substances) customarily ranges between 0.001% to 5%, preferably 0.01% to 4% and more preferably 0.05% to 3%, and most preferably 0.1% to 2% by weight, calculated to the total of the composition C.

The suitable non-limiting examples of the coupling substance if present in the composition A are 5-amino-2-methylphenol, 2-methyl-5-hydroxyethylaminophenol, 2,4,-diamnophenoxyehanol, 2-amino-4-hydroxyethylaminoanisol, 2-methyl-5-amino-6-chlorphenol, 1,3-bis(2,4-diaminophenoxy)propane, 2-bis(2-hydroxyethyl)aminotoluene, 2-amino-5-methylphenol, resorcinol, 2-methyl-resorcinol, 4-chlororesorcinol, 2-amino-4-chlorophenol, 5-amino-4-methoxy-2-methylphenol, 2-aminophenol, 3-amino-phenol, 1-methyl-2-hydroxy-4-aminobenzene, 3-N,N-dimethyl aminophenol, 2,6-dihydroxy-3,5-dimethoxypyridine, 5-amino-3-methylphenol, 6-amino-3-methylphenol, 1,3-diamino-benzene, 1-amino-3-(2'-hy-droxyethylamino)benzene, 1-amino-3-[bis(2'-hy-droxy-ethyl) amino]benzene, α-naphthol, 4,6-dichlororesorcinol, 1,3-diamino-toluene, 4-hydroxy-1,2-methylenedioxy benzene, 1,5-dihydroxy naphthalene, 1,6-dihydroxy naphthalene, 1,7-dihydroxy naphthalene, 2,7-dihydroxy naphthalene, 1-hydroxy-2-methyl naphthalene, 4-hydroxy-1,2-methyldioxy benzene, 2,4-diamino-3-chlorophenol, 5-amino-2-methoxyphenol and/or 1-methoxy-2-amino-4-(2'-hydroxyethyl amino)benzene or the water-soluble salts thereof and mixture thereof.

In the composition C, the coupling substance(s) as reaction partners of the developing substance(s) are present in approximately the same molecular proportions as the developing substances, i.e. at a total concentration in the range of 0.001% to 5%, preferably 0.01% to 4% and more preferably 0.05% to 3%, and most preferably 0.1% to 2% by weight, calculated to the total of the composition C.

The compositions A and/or D and/or C comprise(s) optionally one or more hair direct dyes. Suitable ones are cationic, anionic and nitro dyes. Plant dyes are also suitable for the compositions of the present invention.

Suitable anionic direct dyes are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9, Disperse Violet 1, HC Blue 18, HC Red 18 and HC Yellow 16 and their alkali metal salts such as sodium, potassium. Among those, the most preferred anionic dyestuffs are Acid Red 52, DC Violet 2, DC Red 33, DC Orange 4, DC Red 27, DC Yellow 10, HC Blue 18, HC Red 18 and HC Yellow 16.

Suitable cationic dyes are in principle those available on the market for cosmetic hair colouring applications. For this purpose, special reference is made to the PCT application WO 95/15144 of Ciba-Geigy AG. Some examples to those are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 76, Basic Violet 1, Basic Violet 2, Basic Violet 3, Basic Violet 10, Basic Violet 14, Basic Yellow 57, Basic red 51, Basic Yellow 87, HC Blue 17 and Basic Orange 31. The most preferred ones are Basic red 51, Basic Yellow 87 and Basic Orange 31 sold by BASF, and HC Blue 17.

Suitable nitro dyes are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Plant dyestuffs can also be used alone or in combination with synthetic direct-acting dyestuffs, for example henna (red or black), alkanna root, laccaic acid, indigo, logwood powder, madder root and rhubarb powder, etc.

The composition A and/or D and/or C may comprise one or more hair direct dye at a total concentration of 0.01% to 10%, preferably 0.05% to 7.5% and more preferably 0.1% to 5% by weight calculated to the total of the compositions A, D or C. The composition can also comprise mixtures of several direct dyes, i.e., anionic, cationic and/or nonionic ones. In such a case the dyes may be mixed at any ratio with each other.

The composition C comprises furthermore one or more alkalizing agents, preferably selected from ammonia, alkyl- or alkanolamines according to the general structure

wherein $R_1$, $R_2$, and $R_3$ are same or different H, from $C_1$ to $C_4$, $C_3$ to $C_4$ unsaturated alkyl, $C_3$ to $C_4$ branched alkyl, $C_1$ to $C_4$ hydroxyl alkyl, $C_3$ to $C_4$ unsaturated hydroxyl alkyl, $C_3$ to $C_4$ branched hydroxyl alkyl, with the condition that at least one of $R_1$, $R_2$, or $R_3$ is different from H, wherein the alkalizing agents preferably selected from ammonia, monoethanolamine, and aminomethylpropanol, and particularly suitable one is aminomethylpropanol.

The alkalizing agent is comprised in the composition C at a total concentration of 1% to 20%, preferably 1% to 17.5%, more preferably 2% to 15% and most preferably 2.5% to 13% by weight calculated to the total of the composition C.

The pH of the composition C is in the range of 7.5 to 12, preferably 8.0 to 11, more preferably 8.5 to 10.5 and most preferably 9.0 to 10.5.

The pH of the ready-to-use composition obtained by mixing the composition B, C, and D is in the range of 6.5 to 11, preferably 6.8 to 11, more preferably 8 to 10.5 and most preferably 9.0 to 10.5.

After application of the ready to use dyeing composition onto hair in step e, the dyeing composition is left on the hair for 1 min to 45 min at room temperature or at an elevated temperature up to 45° C. and subsequently rinsed off from hair and the hair is optionally washed with a cleansing composition and dried. The composition D comprises i. one or more carboxylic acids having three or more carboxyl groups and/or their salts, and ii. one or more additional organic acids and/or their salts having one or two carboxyl groups.

Suitable carboxylic acids with three or more carboxyl groups and/or their salts are citric acid, ethylenediamine tetraacetic acid (EDTA), pyromellitic acid and glutamate diacetate. The ethylenediamine tetraacetic acid (EDTA) and/or its salts such a monosodium, disodium, trisodium and tetrasodium salts are the most preferred ones.

Suitable inorganic acids and/or their salts are hydrochloric acid, sulfuric acid, nitric acid, phosphoric acid, and etidronic acid, and suitable organic acids with one or two carboxyl groups and/or their salts are acetic acid, malic acid, lactic acid, glycolic acid, tartaric acid, formic acid, oxalic acid, malonic acid, succinic acid, glutaric acid, adipic acid, maleic acid, and fumaric acid. In the preferred embodiment of the present invention the composition D comprises as the second acid one or more organic acids having one or two carboxyl groups and the most preferred acid is malic acid and/or its salts such as sodium, potassium and ammonium salts.

The composition D comprises the two acids at a total concentration in the range of 10% to 100% by weight, preferably 12.5% to 90%, more preferably 12.5% to 75% by weight and most preferably 12.5% to 60% by weight, calculated to the total of composition D.

The two acids are comprised in the composition D at a weight ratio of first acid (i) to second acid (ii) in the range from 10:1 to 1:250, preferably from 5:1 to 1:150, and more preferably from 2:1 to 1:100 and most preferably 1:50.

The composition D may be in the form of a powder, a dispersion, an emulsion or a solution. In a preferred embodiment of the present invention the composition D is an aqueous composition and preferably has a pH in the range of 1 to 5, preferably 2 to 4, more preferably in the range of 2.5 to 3.6. In the case that the pH must be adjusted to a certain value, the composition D comprises one or more alkalizing agents. The suitable alkalizing agents are the same as described above for composition C. Preferred alkalizing agents for composition D are ammonia, monoethanolamine, and aminomethylpropanol, and particularly suitable one is aminomethylpropanol.

The alkalizing agent is comprised in the composition D at a total concentration of 1% to 20%, preferably 1% to 15%, more preferably 2% to 12.5% and most preferably 2.5% to 10% by weight calculated to the total of the composition D.

In a further preferred embodiment of the present invention, the composition D comprises one or more thickening polymers selected from anionic, nonionic, cationic and amphoteric polymers, preferably selected from polymers with a viscosity of at least 500 mPa·s measured at a polymer concentration of 1% by weight in water and at 20° C. with a Brookfield viscometer, such as at 10 rpm for 1 min, with an appropriate spindle.

Suitable polymers are cellulose polymers, alginates, polysaccharides and acrylic acid polymers, preferably methyl cellulose, ethyl cellulose, hydroxyethylcellulose, methylhydroxyethylcellulose, methylhydroxypropylcellulose, carboxymethyl cellulose, alginic acids, sodium alginates, ammonium alginates, calcium alginates, gum arabic, guar gum or xanthan gum, dehydroxanthan gum or acrylic acid polymers known with the CTFA adopted name Carbomer and its derivatives.

The preferred polymers are dehydroxanthan gum, xanthan gum, and polymeric anionic thickeners Carbomer and its derivatives. The particularly preferred thickening agent is dehydroxanthan gum. The thickening agents are preferably comprised in the composition C at a total concentration in the range of 0.1% to 5%, preferably, 0.2% to 3%, more preferably 0.25% to 2.5% and most preferably 0.3% to 2% by weight calculated to the total of the composition D.

In a further embodiment of the present invention, the composition D may comprise optionally one or more direct dyes as defined above for the composition C at the concentrations defined there as well.

In a still further embodiment of the present invention, the anhydrous composition A may comprise optionally one or more direct dyes as defined above for the composition C at the concentrations defined there as well.

Any of the compositions A, B, C or D may comprise one or more of the commonly used hair conditioning compounds. These compounds are for example fatty alcohols, surfactants such as anionic, nonionic, cationic and amphoteric ones, ubiquinones, ceramides, organic solvents, lipophilic ingredients such as vegetable oils, mineral oils, silicones, fatty acid fatty alcohol esters, preservatives, amino acids, and polyols. It should be noted that these compounds are optionally comprised in the any of the compositions and their incompatibility must be carefully considered prior to addition in the compositions.

Any of the composition may comprise one or more fatty alcohols. In particular the compositions B, C and D may be aqueous compositions and may further be in the form of an emulsion and then comprise preferably one or more fatty alcohols. Suitable fatty alcohols are the ones with the chain length of 14 to 22 C atoms which may be saturated or unsaturated, linear or branched which may as well be substituted. Non-limiting examples are myristyl alcohol, cetyl alcohol, stearyl alcohol, behenyl alcohol and cetostearyl alcohol.

The total concentration of fatty alcohol is in the range from 0.5% to 20%, preferably 1% to 15% by weight, calculated to the total of each composition.

Compositions A, B, C and/or D according to the present invention may comprise surfactants selected from anionic, nonionic, amphoteric and/or cationic surfactants. The anionic, nonionic, amphoteric surfactants are used generally as emulsifier or solubilizer whereas the cationic surfactants are at the same time particularly used as hair conditioners.

Anionic surfactants suitable are in principal known from the cleansing compositions. These are anionic surfactants of the sulfate, sulfonate, carboxylate and alkyl phosphate type, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates.

Additional anionic surfactants useful within the scope of the invention are α-olefin sulfonates or the salts thereof, and in particular alkali salts of sulfosuccinic acid semiesters, for example, the disodium salt of monooctyl sulfosuccinate and alkali salts of long-chain monoalkyl ethoxysulfosuccinates.

Suitable surfactants of the carboxylate type are alkyl polyether carboxylic acids and the salts thereof as well as alkyl amido polyether carboxylic acids and salts thereof. Such products have been known for some time and are on the market, for example, under the trade name "AKYPO®" and "AKYPO-SOFT®".

Also useful are $C_8$-$C_{20}$-acyl isethionates, alone or in admixture with other anionic surfactants, as well as sulfofatty acids and the esters thereof.

Further suitable anionic surfactants are also $C_8$-$C_{22}$-acyl aminocarboxylic acids or the water-soluble salts thereof. Especially preferred is N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in admixture with the above-named anionic surfactants.

It is also possible to use mixtures of several anionic surfactants.

Further surfactants suitable are nonionic surfactants. Non-limiting examples are long-chain fatty acid mono- and dialkanolamides, such as coco fatty acid mono- or diethanolamide and myristic fatty acid mono or diethanolamide, stearic acid mono or diethanolamide, alkyl polyglucosides with an alkyl group of 8 to 18 carbon atoms, and with 1 to 5 glucoside units, sorbitan esters, such as polyethylene glycol sorbitan stearic acid ester, palmitic acid ester, myristic acid ester, or lauric acid ester, and fatty acid polyglycol esters or poly-condensates of ethyleneoxide and propyleneoxide, as they are on the market, for example, under the trade name "Pluronics$^R$", as well as fatty alcohol ethoxylates, $C_{10}$-$C_{22}$-fatty alcohol ethoxylates, known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16": The average degree of ethoxylation thereby ranges between about 2 and about 100, preferably about 10 and about 30.

Suitable amphoteric surfactants are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate have also proven suitable.

Suitable cationic surfactants are according to the general structure $$R_6-\overset{\overset{R_9}{|}}{\underset{\underset{R_5}{|}}{N^+}}-R_4 \quad X^-$$

where $R_5$ is a saturated or unsaturated, branched or linear alkyl chain with 8-22 C atoms or $$R_7\ CO\ NH\ (CH_2)_n$$

where $R_7$ is saturated or unsaturated, branched or linear alkyl chain with 7-21 C atoms and n has typical value of 1-4 or $$R_8\ CO\ O\ (CH_2)_n$$

where $R_8$ is saturated or unsaturated, branched or linear alkyl chain with 7-21 C atoms and n has typical value of 1-4, and $R_4$ is H or unsaturated or saturated, branched or linear alkyl chain with 1-22 C atoms or $$R_7\ CO\ NH\ (CH_2)_n$$

or $$R_8\ CO\ O\ (CH_2)_n$$

where $R_7$, $R_8$ and n are same as above.

$R_9$ and $R_6$ are H or lower alkyl chain with 1 to 4 Carbon atoms, and X is typically chloride, bromide, methosulfate.

Typical examples of those ingredients are cetyl trimethyl ammonium chloride, stearyl trimonium chloride, dipalmitoyl dimonium chloride, distearyl dimethyl ammonium chloride, stearamidopropyl trimonuim chloride, dioleoylethyl dimethyl ammonium methosulfate, dioleoylethyl hydroxyethylmonium methosulfate.

The concentration of one or more total surfactants in any of the compositions A, B, C or D is in the range of 0.1% to 20%, preferably 0.2% to 15% and most preferably 0.2% to 10% by weight, calculated to the total of each composition.

The compositions A, B, C or D may further comprise lipophilic ingredients such as vegetable oils, for example, jojoba oil or any other; liquid paraffins, especially paraffinum perliquidum and paraffinum subliquidurn, silicones for example linear polysiloxanes such as dimethicones with various consistency and dimethiconols, aminated silicones with primary, secondary, tertiary or quaternary ammonium groups such as amodimethicone, polysilicone 9, and quaternium 80, cyclic silicones such as cyclomethicones, arylated silicones such as phenyl trimethicone; fatty acid esters such as octyl palmitate, isocetyl palmitate, isopropyl palmitate and octyl stearate, $C_{10}$-to $C_{36}$-fatty acid triglycerides, as well as their mixtures. Total concentration of these lipophilic compounds is in the range of 0.5% to 20% by weight, preferably from 1% to 15% by weight, and more preferably from 2% to 10% by weight, calculated to the total of each composition.

The compositions A, B, C or D can also comprise cationic polymers as conditioning and/or thickening agents. Those are cationic cellulose type polymers know as Polymer JR type from Amerchol such as Polyquaternium 10 or cationic guar gum known with trade name Jaguar from Rhône-Poulenc and chemically for example Guar hydroxypropyl trimonium chloride. Furthermore, chitosan and chitin can also be included in the compositions as cationic natural polymers.

Furthermore, it has been found suitable those cationic polymers known with their CTFA category name Polyquaternium. Typical examples of those Polyquaternium 4, Polyquaternium 6, Polyquaternium 7, Polyquaternium 10, Polyquaternium 11, Polyquaternium 16, Polyquaternium 22, Polyquaternium 24, Polyquaternium 28, Polyquaternium 30, Polyquaternium 37, Polyquaternium 36, Polyquaternium 46, Polyquaternium 67, and Polyquaternium 72.

As well those polymers known with their CTFA category name Quaternium are suitable. Those are for example Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-82, Quaternium-83 and Quaternium-84.

The total concentration of cationic polymers may be in the range of 0.1-7.5% by weight, preferably 0.3-5% by weight and more preferably 0.5-2.5% by weight, calculated to total of each composition Composition A, B, C or D may comprise one or more ceramide compound, such as the one according to general formula 1

Formula 1

$$\begin{array}{c} R_{11}-O-CH_2 \\ | \\ CHOH \\ | \\ R_{12}-\underset{\underset{O}{\|}}{C}-\underset{\underset{R_{13}}{|}}{N}-CH_2 \end{array}$$

where $R_{11}$ and $R_{12}$ are independent from each other an alkyl- or alkenyl group with 10 to 22 carbon atoms, $R_{13}$ is alkyl or hydroxyl alkyl with 1 to 4 carbon atoms group and n is a number between 1 to 6, preferably 2 or 3. Preferred compound according to the above chemical structure is cetyl-PG-hydroxyethylpalmitamide. Concentration of ceramide type of compounds ranges from 0.01 to 2%, preferably 0.01 to 1% by weight calculated to total or each composition.

The compositions A, B, C or D may comprise ubiquinone of the formula 2:

Formula 2 wherein n is a number from 1 to 10. The concentration of ubiquinone can vary between 0.001% and 10% by weight, calculated to the total of each composition.

The compositions B, C, and/or D may comprise one or more organic solvent such as 2-phenoxyethanol, benzyl alcohol, 2-phenylethanol and 2-benzyloxyethanol. Suitable aliphatic alcohols are ethanol, isopropanol, propanol, n-butanol, isobutanol, t-butanol and 1-pentanol. Concentration of one or more organic solvent is in the range of 0.1% to 15%, preferably 0.5% to 12.5% and more preferably 1% to 10% and most preferably 1% to 7.5% by weight calculated to the total of each composition.

The compositions A, B, C and/or D may further comprise one or more amino acids, preferably at a concentration in the range of 0.01% to 5%, preferably 0.1% to 3% and more preferably 0.2% to 2.5% and most preferably 0.25% to 2% by weight calculated to the total of each composition.

Suitable ones are all of the known amino acids such as, arginine, alanine, asparagine, glutamine, glycine, histidine, leucine, lysine, methionine, phenylalanine, proline, serine, threonine, tryptophan, tyrosine and valine.

The compositions A, B, C and/or D may further comprise one or more polyol(s), preferably at a concentration in the range of 0.01% to 5%, preferably 0.1% to 3% and more preferably 0.2% to 2.5% and most preferably 0.25% to 2% by weight calculated to the total of each composition. Suitable ones are propylene glycol, dipropylene glycol, glycerine, panthenol and its derivatives.

The compositions A, B, C and/or D may further comprise any known preservatives if necessary.

The following examples are to illustrate the invention, but not to limit it.

EXAMPLE 1

The Composition A

| | % by weight |
|---|---|
| Ammonium persulfate | 21.00 |
| Potassium persulfate | 36.00 |
| Sodium metasilicate | 11.00 |
| Diatomaceous Earth | 21.00 |
| Aerosil 380 | 1.00 |
| Liquid paraffin | 10.00 |

The above composition was prepared by combining all powder components and by mixing in a suitable mixer until homogeneity was achieved.

The Composition B

| | % by weight |
|---|---|
| Hydrogen peroxide | 9.00 |
| Cetyl stearyl alcohol | 1.70 |
| Phosphoric acid | q.s. to pH 3.0 |
| Sodium lauryl sulfate | 0.20 |
| Salicylic acid | 0.10 |
| Water | ad 100.00 |

The Composition C

| | % by weight |
|---|---|
| Cetearyl alcohol | 10.0 |
| Cocamide MEA | 4.0 |
| Sodium lauryl sulphate | 1.5 |
| Propylene glycol | 2.0 |
| Cetyltrimonium chloride | 0.5 |
| 2,5,6-Triamino-4-hydroxypyrimidine sulfate | 0.01 |
| 2,5-Diaminotoluene sulfate | 0.55 |
| 4-Chlororesorcinol | 0.17 |
| Resorcinol | 0.05 |
| 3-Aminophenol | 0.03 |
| Sodium sulfite | 1.0 |
| Aminomethyl propanol | 2.0 |
| Ammonium hydroxide | q.s. to pH 10.0 |
| Fragrance, preservative | q.s. |
| Water | to 100 |

The Composition D

| | % by weight |
|---|---|
| EDTA tetrasodium salt | 1.0 |
| Malic acid | 13.0 |
| Aminomethylpropanol | 6.0 |
| Hydroxypropyl xanthan gum | 0.6 |
| Cetrimonium chloride | 0.1 |
| Preservative | q.s. |
| Water | to 100 |

The pH value of the above composition D was 3.5±0.1.

The compositions A, B and D were mixed at a weight ratio of A, B and D 1:2:0.2. The resulting composition had a pH of approximately 9.5. Caucasian hair streaks of 25 cm length were obtained from International Hair Importers & Products Inc., Glendale, N.Y., USA. The composition was applied the hair streaks and left on the hair for 30 min at ambient temperature and rinsed off from hair and the hair was towel dried.

Subsequently, the compositions B, C and D were mixed at a weight ratio of B, C and D 2:1:0.2. The resulting composition had a pH of approximately 9.5. The composition was applied onto the same human hair streaks and left on the hair for 30 min at ambient temperature. Afterwards the hair was rinsed off, then shampooed with a Dualsenses Color shampoo, and dried (inventive process).

For comparative purposes, the same steps as described above were carried out without using the composition D. Instead of composition D the same amount of water was added. The resulting composition had a pH of approximately 9.9 (mixture of compositions A and B and water) and approximately 9.8 (mixture of compositions C and B and water). The compositions were applied onto human hair as described above in subsequent order and left on the hair for 30 min (each composition) at ambient temperature, rinsed off from hair, then shampooed with a Dualsenses Color shampoo and dried (comparative process).

Color durability was investigated by incubating the hair streaks in a shaking bath for 20 min at 30° C. The water bath was filled with an aqueous solution of sodium laureth sulfate at a concentration of 3.5% by weight, calculated to the total of the water bath solution. Upon incubation, the hair streaks were rinsed with water and towel dried. Color results were measured prior to incubation and upon incubation by spectrophotometrical analysis with a Datacolor 45G CT instrument delivered from Datacolor Inc., Lawrenceville, N.J., USA. Based on the CIE*Lab color space results obtained by the measurements, $\Delta E_{ab}$ values for color difference were calculated according to equation (1):

$$\Delta E_{ab} = \sqrt{(L_2-L_1)+(a_2-a_1)+(b_2-b_1)} \qquad \text{Equation 1}$$

The CIE*Lch values were measured with the same instrument and were reported for comparison purposes as well.

| Treatment | Inventive Process | | | | | Comparative Process | | | | |
|---|---|---|---|---|---|---|---|---|---|---|
| group | L | a | b | c | h | L | a | b | c | h |

| | | | | | | | | | | |
|---|---|---|---|---|---|---|---|---|---|---|
| Before (1) | 41.42 | 35.57 | 27.78 | 45.13 | 38.00 | 42.15 | 36.56 | 29.47 | 46.96 | 38.87 |
| After (2) | 50.11 | 27.74 | 26.28 | 38.21 | 43.45 | 54.09 | 23.99 | 23.98 | 33.92 | 45.00 |
| | $\Delta$ L | $\Delta$ a | $\Delta$ b | $\Delta$ c | $\Delta$ h | $\Delta$ L | $\Delta$ a | $\Delta$ b | $\Delta$ c | $\Delta$ h |
| $\Delta\,E_{ab}$ | 8.70 | −7.82<br>11.8 | −1.50 | −6.92<br>— | 5.45 | 11.94 | 12.57<br>18.2 | −5.48 | −13.03<br>— | 4.26 |

The results clearly showed that the inventive process delivered lower $\Delta\,E_{ab}$ results compared to the comparative process which corresponds to a lower change and higher durability of the color upon incubation. Consequently the inventive process led to a more long-lasting color result. Furthermore, color vibrancy (c value) strongly dropped upon treatment of the streak with the comparative process by approximately 13 color units, whereas the inventive process stabilized the color vibrancy at about half of that value. In conclusion the presented data clearly showed the superior performance of the inventive process compared to the state-of-the-art process.

Similar results were obtained with the following compositions (composition D) when used with the Compositions A and B of the Example 1.

EXAMPLE 2

The Composition D

| Component | % by weight |
|---|---|
| AMP | 6.0 |
| EDTA tetrasodium salt | 3.0 |
| Malic acid | 13.0 |
| Lactic acid | 4.0 |
| Hydroxypropyl xanthan gum | 0.6 |
| Polyquaternium-10 | 0.1 |
| Water | to 100 |

The pH value of the above composition D was 3.4±0.1.

EXAMPLE 3

The Composition D

| Component | % by weight |
|---|---|
| Monoethanolamine (MEA) | 2.7 |
| EDTA tetrasodium salt | 5.0 |
| Malic acid | 15.0 |
| Hydroxypropyl xanthan gum | 0.6 |
| Panthenol | 0.1 |
| Water | To 100 |

The pH value of the above composition D was 3.3±0.1.

EXAMPLE 4

The Composition D

| Component | % by weight |
|---|---|
| AMP | 6.0 |
| Citric acid | 5.0 |
| Maleic acid | 15.0 |
| Hydroxypropyl xanthan gum | 0.6 |
| Behenamidopropyl trimonium chloride | 0.2 |
| Water | to 100 |

The pH value of the above composition D was 1.4±0.1.

EXAMPLE 5

The Composition D

| Component | % by weight |
|---|---|
| MEA | 2.0 |
| Lactic acid | 15.0 |
| Citric acid | 6.0 |
| Dehydroxyxanthan gum | 0.6 |
| Polyquaternium-67 | 0.1 |
| Water | to 100 |

The pH value of the above composition D was 2.7±0.1.

EXAMPLE 6

The Composition A

| | % by weight |
|---|---|
| Ammonium persulfate | 21.00 |
| Potassium persulfate | 36.00 |
| Sodium metasilicate | 11.00 |
| Diatomaceous Earth | 19.00 |
| Aerosil 380 | 1.00 |
| HC Blue 18 | 1.00 |
| HC red 18 | 1.00 |
| Liquid paraffin | 10.00 |

The hair was treated with the above composition using the compositions B and D of the Example 1 as described under Example 1. Subsequently the hair was dyed oxidatively with the compositions of Example 1 as described thereunder. It was observed that the hair was bleached and dyed effectively into intensive red color. Exclusion of the composition D resulted in loss of color brilliance and combability.

EXAMPLE 7

The Composition D

| | % by weight |
|---|---|
| EDTA tetrasodium salt | 1.0 |
| Malic acid | 13.0 |
| Aminomethylpropanol | 6.0 |

| | % by weight |
|---|---|
| Basic Red 51 | 1.00 |
| HC Red 18 | 1.00 |
| Hydroxypropyl xanthan gum | 0.6 |
| Cetrimonium chloride | 0.1 |
| Preservative | q.s. |
| Water | to 100 |

The pH value of the above composition D was 3.5±0.1.

Hair was treated with the above composition D using the compositions A, B and C of the example 1 as described under the Example 1. It was observed that the hair was bleached and dyed effectively into intensive red color. Exclusion of the composition D resulted in loss of color brilliance and combability.

EXAMPLE 8

The Composition D (Powder)

| | % by weight |
|---|---|
| EDTA tetrasodium salt | 7.0 |
| Malic acid | 93.0 |

1 g of the composition D above was added to the mixture of 10 g of composition A and 20 g of composition B (1 to 2) of the example 1. After mixing thoroughly, the resulting composition was applied onto hair and rinsed off after leaving on the hair for 30 min and the hair was towel dried. Subsequently, 1 g of the above composition D was added to the mixture of 20 g of composition B and 20 g of composition C (1 to 1) of the Example 1 and applied onto hair. After leaving the composition on the hair for a period of 30 min the hair was rinsed off and shampooed once and dried. It was observed that the hair was effectively bleached and dyed.

EXAMPLE 9

The Composition D

| | % by weight |
|---|---|
| EDTA monosodium salt | 1.0 |
| Malic acid | 13.0 |
| Aminomethylpropanol | 6.0 |
| Hydroxypropyl xanthan gum | 0.6 |
| Cetrimonium chloride | 0.1 |
| Preservative | q.s. |
| Water | to 100 |

The pH of the above composition D is approximately 3.1.

EXAMPLE 10

The Composition D

| | % by weight |
|---|---|
| EDTA disodium salt | 1.0 |
| Malic acid | 13.0 |
| Aminomethylpropanol | 6.0 |
| Hydroxypropyl xanthan gum | 0.6 |
| Cetrimonium chloride | 0.1 |
| Preservative | q.s. |
| Water | to 100 |

The pH of the above composition D is approximately 3.2.

EXAMPLE 11

The Composition D

| | % by weight |
|---|---|
| EDTA trisodium salt | 1.0 |
| Malic acid | 13.0 |
| Aminomethylpropanol | 6.0 |
| Hydroxypropyl xanthan gum | 0.6 |
| Cetrimonium chloride | 0.1 |
| Preservative | q.s. |
| Water | to 100 |

The pH of the above composition D is approximately 3.4.

The invention claimed is:

1. A process for treating hair, the process comprising steps of:
   a. applying a first mixed aqueous composition to hair,
      wherein the first mixed aqueous composition is obtained from mixing two compositions A and B,
      wherein the composition A is an anhydrous composition comprising one or more persalts and one or more alkalizing agents,
      wherein the composition B is an aqueous composition comprising one or more oxidizing agents, and has a pH in the range of 1.5 to 5,
      wherein the first mixed aqueous composition, consisting of compositions A and B, has an alkaline pH in the range from 8 to 11,
   b. leaving the first mixed aqueous composition on the hair for a period of 1 minute to 45 minutes,
   c. rinsing the first mixed aqueous composition off the hair and towel drying the hair,
   d. optionally drying the hair,
   e. applying a second mixed aqueous composition onto the hair,
      wherein the second mixed aqueous composition is obtained from mixing the two compositions C and B,
      wherein the composition C is an aqueous composition comprising one or more hair dyes and one or more alkalizing agents and has an alkaline pH in the range of 7.5 to 12,
   f. leaving the second mixed aqueous composition on the hair for a period of 1 minute to 45 minutes, and
   g. rinsing the second mixed aqueous composition off the hair,
   wherein the at least one of composition A in step a., composition B in step a., composition B in step e., and composition C in step e. is mixed with a composition D immediately before application onto hair for obtaining at least one ready-to-use composition,
   wherein the composition D comprises:
      i. one or more carboxylic acids and/or their salts having three or more carboxyl groups; and
      ii. one or more organic additional acids and/or their salts having one or two carboxyl groups, wherein the composition D comprises the acids of i) and ii) and/or their salts at a total concentration of 10% to 100% by weight calculated to the total of composition D, wherein the at least one ready-to-use composition has a pH in the range from 6.5 to 11 and comprises the acids and/or their salts at a total concentration in the range from 1% to 10% by weight calculated to the total of each of the at least one ready to use composition.

2. The process according to claim 1, wherein the carboxylic acid with three or more carboxyl groups is selected from citric acid, ethylenediamine tetraacetic acid (EDTA), pyromellitic acid and glutamate diacetate, and the organic acid with one or two carboxyl groups is selected from the group consisting of acetic acid, malic acid, lactic acid, glycolic acid, tartaric acid, formic acid, oxalic acid, malonic acid, succinic acid, glutaric acid, adipic acid, maleic acid, and fumaric acid, and wherein the composition D comprises the first acid (i) and the second acid (ii) at a weight ratio (i)/(ii) in the range from 10:1 to 1:250.

3. The process according to claim 2, wherein the composition D is a powder, a dispersion, an emulsion or a solution.

4. The process according to claim 3, wherein the pH of composition D is in the range from 1 to 5.

5. The process according to claim 2, wherein the carboxylic acid with 3 or more carboxyl groups is EDTA and/or its salts.

6. The process according to claim 2, wherein the organic acid with one or two carboxyl groups is malic acid and/or its salts.

7. The process according to claim 4, wherein the composition C further comprises, as one or more hair dye, one or more oxidative dye precursors selected from p-phenylendiamines, p-aminophenols, and heterocyclic compounds, and optionally one or more coupling substances selected from resorcinols, m-aminophenols, m-phenylendiamines, pyridines, and naphthols.

8. The process according to claim 4, wherein at least one of composition A, composition C and composition D further comprises one or more direct hair dye selected from cationic, anionic, nitro dyes and their mixtures.

9. The process according to claim 7, wherein at least one of composition C and composition D further comprises at least one alkalizing agent selected from ammonia, alkyl- or alkanolamines according to the general structure

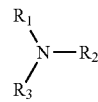

wherein $R_1$, $R_2$, and $R_3$ are same or different H, from $C_1$ to $C_4$, $C_3$ to $C_4$ unsaturated alkyl, $C_3$ to $C_4$ branched alkyl, $C_1$ to $C_4$ hydroxyl alkyl, $C_3$ to $C_4$ unsaturated hydroxyl alkyl, $C_4$ to $C_4$ branched hydroxyl alkyl, with the condition that at least one of $R_1$, $R_2$, or $R_3$ is different from H.

10. The process according to claim 9, wherein the one or more alkalizing agents of composition A is selected from sodium metasilicate, ammonium salts, carbonate salts and bicarbonate salts.

11. The process according to claim 7, wherein at least one selected from composition A, composition B, composition C and composition D comprises one or more ingredients, selected from fatty alcohols, surfactants, ubiquinones, ceramides, reducing agents, organic solvents, silicones, antioxidants, preservatives, amino acids, polyols.

12. The process according to claim 1, wherein the one or more persalts of composition A are selected from sodium persulfate, potassium persulfate, and ammonium persulfate, and are present at a concentration in the range of 10% to 80% by weight calculated to the total of composition A.

13. The process according to claim 1, wherein the composition D further comprises one or more thickening polymers with a viscosity of at least 500 mPa·s measured at a polymer concentration of 1% by weight in water and at 20° C. with a Brookfield viscometer, at 10 rpm for 1 minute, with an appropriate spindle.

14. The process according to claim 13, wherein the thickening polymer is selected from dehydroxanthan gum, xanthan gum, and polymeric anionic thickeners.

15. A kit for hair comprising the compositions A, B, C and D according to claim 1.

16. The process according to claim 11, wherein the surfactants are selected from anionic, nonionic, cationic and amphoteric ones.

17. The process according to claim 11, wherein the silicones are selected from linear polysiloxanes, aminated silicones, cyclic silicones, and arylated silicones.

18. The process according to claim 13, wherein the one or more thickening polymers is selected from anionic, nonionic, cationic and amphoteric polymers.

* * * * *